US00PP08336P

United States Patent [19]

Weinberger

[11] Patent Number: Plant 8,336

[45] Date of Patent: Aug. 10, 1993

[54] NECTARINE TREE CV. SUNECTNINETEEN

[75] Inventor: John H. Weinberger, Fresno, Calif.

[73] Assignee: Sun World, Inc., Indio, Calif.

[21] Appl. No.: 841,043

[22] Filed: Feb. 25, 1992

[51] Int. Cl.[5] ..... A01H 5/00

[52] U.S. Cl. ..... Plt./41.1

[58] Field of Search ..... Plt. 41.1

*Primary Examiner*—James R. Feyrer

*Attorney, Agent, or Firm*—Synnestvedt & Lechner

[57] ABSTRACT

A nectarine tree characterized by its large fruit, ripening two weeks ahead of the "Red Jim" nectarine and its brighter, smoother red blush than "Red Jim" and other nectarines ripening in the same general time frame.

2 Drawing Sheets

This invention relates to the discovery and asexual propagation of a new variety of hybrid nectarine tree, *Prunus persica* cv. Sunectnineteen. The tree is a late ripening nectarine with a bright red blush and is cultivated for the fresh fruit market. It was discovered and asexually propagated by John H. Weinberger near Fresno, Calif., and has as its seed parent Sunecteight (U.S. Plant Pat. No. 4,894) and fertilization was accomplished by open pollination. The selected open pollinated seedling was asexually propagated by budding.

The new variety cv. Sunectnineteen may be distinguished from other presently commercially significant nectarine cultivars that ripen at about the same time by the following combination of characteristics: Sunectnineteen ripens approximately two weeks earlier than the Red Jim nectarine (U.S. Plant Pat. No. 4,518). It also possesses a brighter, smoother red blush than Red Jim and other nectarines that ripen during the same general time frame.

Among the characteristics which distinguish the new variety of nectarine tree from its seed parent are the following: the fruit of the Sunectnineteen variety ripens about one month later than its seed parent. The fruit of Sunectnineteen displays a superior red blush, is rounder and more symmetrical in shape than Sunecteight.

The pollen parent of the new variety is unknown.

The above enumerated distinguishing characteristics are held through succeeding asexual propagations, for example by grafting.

Figure 1:
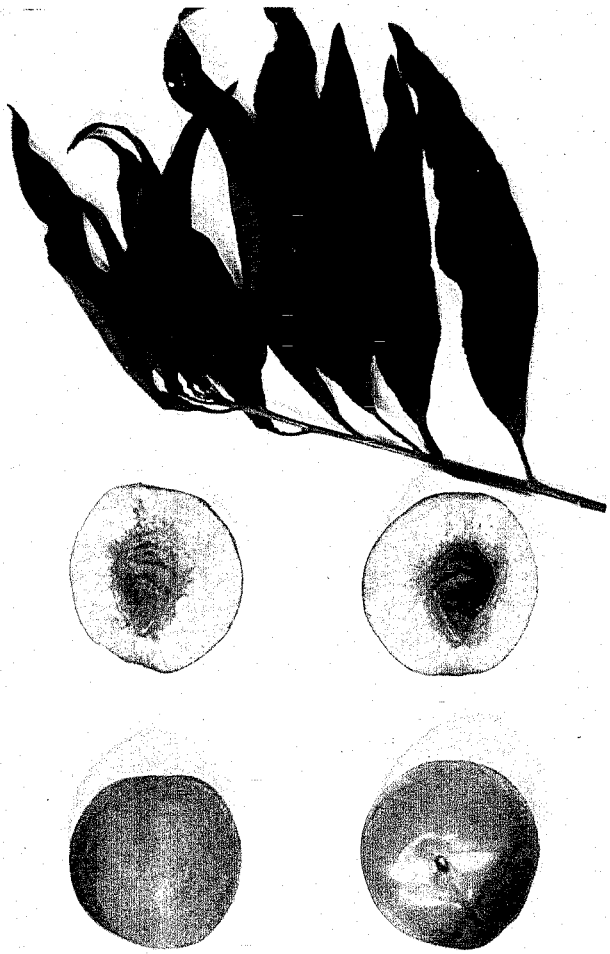

In the accompanying drawings, FIG. 1 illustrates, in full color, a typical stem and mature leaves of the new nectarine tree and the ripe fruit as viewed from the stem end and in profile. The drawing also illustrates the fruit sectioned in half from end to end, one of the fruit sections is shown with the stone in place in the flesh and the other section is shown with the stone removed from the flesh.

Figure 2:
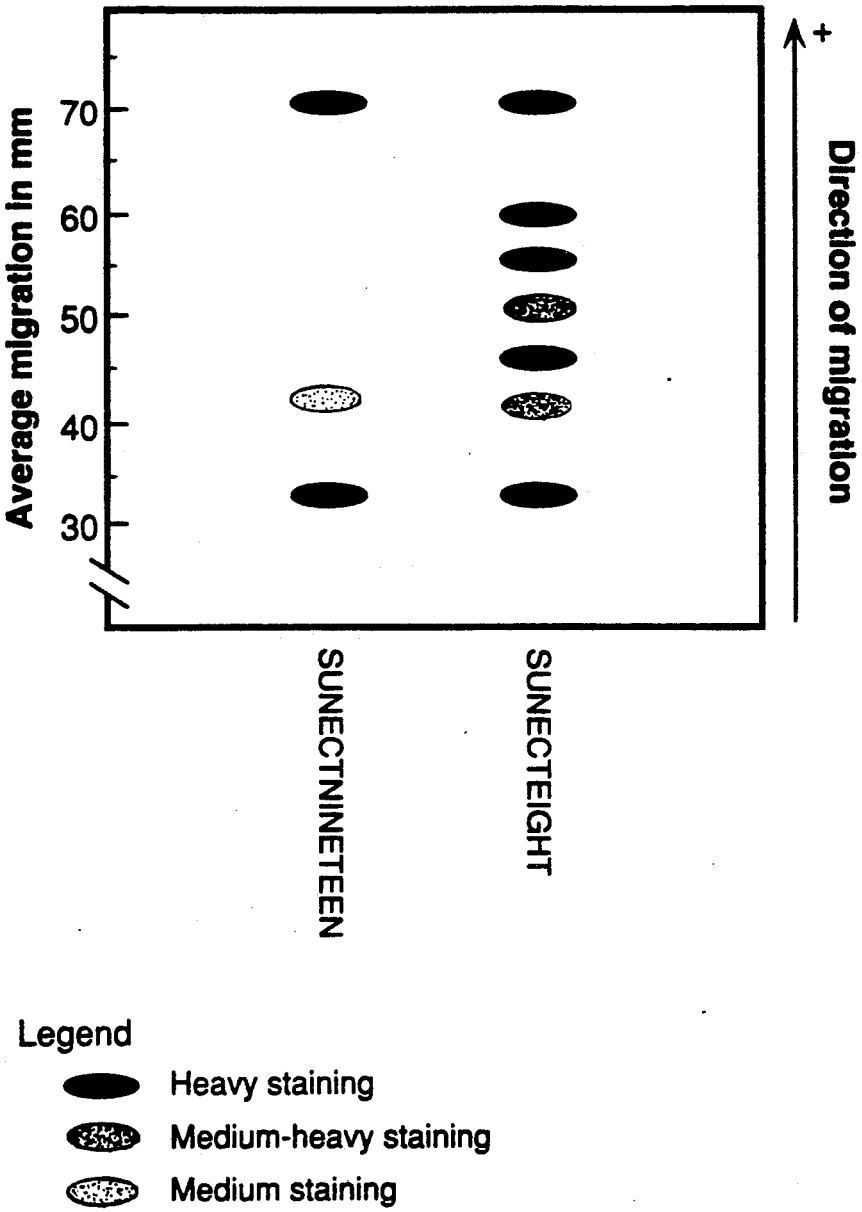

FIG. 2 illustrates the Malate dehydrogenase banding patterns of the Sunecteight and Sunectnineteen varieties after starch gel electrophoresis.

Throughout this specification, color names beginning with a small letter signify that the name of that color, as used in common speech, is aptly descriptive. Color names with capital letters designate values based upon the R.H.S. Colour Chart, published by The Royal Horticultural Society, London, England.

The descriptive matter which follows pertains to the new nectarine variety budded to Nemared rootstock and grown in the vicinity of Wasco, Kern County, Calif. and is believed to apply to plants of the variety grown in similar conditions of soil and climate elsewhere.

TREE

The tree is of medium size and medium vigor. It is semi-upright in habit. The foliage is dense. The trees are hardy, regular bearers and productive.

The trunk is of medium thickness and the bark medium in texture. The branches are medium in caliper, have a smooth surface texture and gives a semi-glossy surface appearance. There are numerous medium-sized lenticels.

LEAVES

In general, leaves are of medium size, having an average length of about 13.1 cm. and an average width of about 2.6 cm. Leaves are lanceolate in outline and upfolded in profile. Leaf blade tips curve downwardly at an acute angle. The serrate leaf margins undulate slightly. The leaf apex is cuspidate; the leaf base is V-shaped. Leaves are thin in thickness. Leaf color on the upper surface is about Yellow-Green 146B. The upper leaf surface is smooth, with no pubescence and weakly glossy, giving a dull surface appearance. The lower leaf surface is about Yellow-Green 146D in color, weakly glossy and no pubescence is present. The lower leaf surface is smooth in texture and has a dull appearance.

The petiole is of medium length and medium thickness. There are usually two small sized glands that are globose in shape oppositely positioned on the leaf base. Glands are about Yellow-Green 151B in color. Stipules are deciduous.

Wood (leaf) buds are medium in size and conical in shape. The position, relative to the shoot, is slightly held out, their support is of medium size and not decurrent. The time of bud burst is medium.

On flowering shoots, anthocyanin of medium intensity is present. The shoots are of medium thickness, have a medium internode length with a medium density of buds on one year old shoots.

FLOWERS

Flower buds are, in general, hardy, of medium size and length, plump in shape and freely positioned. Pubescence is absent and the flowers are about Grayed-Orange 165A in color.

Flowers attain full bloom in medium time—on the average (in 1990 this was about March 8) in the vicinity of Wasco, Calif. Blooms have a duration of about 10 days. The fully opened flower is large in size—about 4.7 cm., rosaceous in shape and the petals are overlapping. The fully opened flowers are Red-Purple 65C in color.

The peduncle is of short length, medium thickness and pubescence is absent.

The receptacle is of medium depth. Pubescence is absent on the inner surface at white bud stage. The outer surface exhibits some pubescence.

Sepals are adpressed to petals, ovate in shape and pubescence is absent on the inner surfaces and present on outer surfaces.

None of the flowers has exhibited double sepals.

Petals are large in size (about 2.2 cm. in width) elliptical in shape, have a short claw length, medium wavy margins and a medium base angle. The division of the upper margins is entire and pubescence is absent on both inner and outer surfaces and both surfaces are Red-Purple 65C in color.

The stigma is positioned above the anthers and are about Orange 25C just before dehiscence.

Pollen is about Yellow-Orange 14D.

Stamens are perigynously positioned.

Pistils: there is always at least one.

Pubescence is absent in ovaries and styles.

FRUIT

The fruit, as described, was eating ripe. The size of the fruit of that stage of its development is large but slightly variable in size, having an axial diameter of about 7.25 cm. and a transverse diameter in the suture plane of about 7 cm. At right angles to the suture plane, the measurement is about 6.75 cm., i.e., a slightly variable, unsymmetrical generally oblong shape. The position of the maximum diameter is towards the middle. The fruit is asymmetric about the suture line. Fruit ripens late in the season and is eating ripe about July 29th.

The suture is distinct but shallow and has a slightly noticeable depression beyond the pistil point. The ventral surface is slightly rounded, lipped towards the apex and with unequal lips. The pistil base is persisting. There is no pubescence at the apex.

The stem cavity is abrupt and circular in shape. The depth of the cavity is about 1.5 cm., and its width about 2.6 cm. No markings are present. The base of the fruit is rounded and its apex is depressed in shape. The pistil point is apical in shape.

The stem is of medium length (about 0.9 cm.), and glabrous and adheres strongly to the stone.

The skin, which is of medium thickness and of medium texture and is tenacious to the flesh. Roughness and reticulation are absent. The skin shows no tendency to crack during the dry season. Skin color is about Red 46A. Down is wanting and a bloom is absent.

The color of the flesh is about Yellow-Orange 16B. The surface surrounding the pit cavity and going into flesh from pit about 4 cm. is about Red-Purple 59A in color. The amygdalin is wanting and juice is moderate. The flesh has a medium sugar content. Flesh is firm, fine and crisp in texture. Fibers are few in number, fine and tender. Fruit ripens evenly first at apex and produces fruit of good eating quality. The flavor is sub-acid and delicate. Aroma is wanting. The stone/flesh ratio is about 9.6/118 grams.

The stone clings adhering to flesh over its entire surface. Fibers of the stone are long. The stone is of medium size about 3.6 cm. in length and about 2.6 cm. in breadth. The width at the stalk end of the stone is about 0.4 cm. and about 2.3 cm. in thickness. The form of the stone in profile is generally obovoid. The form in ventral view is sub-globular. The stone's base is straight. Its apex is nearly rounded and slightly flattened on the left side. The hilum is narrow. The position of the stone's maximum breadth is toward the pistil end and the sides are slightly unequal. The surface of the stone is regularly furrowed near base and has elongated pits from base to above center. There is no outgrowing keel. The ridges are rounded. The ventral stone edge is thick and does not have wings. The dorsal stone edge has medium shallow, narrow grooves; ridges are continuous on both sides. The color of the stone is about Grayed-Orange 176A. The stone does not tend to split during the dry season.

In addition to the foregoing biological and morphological description and to provide a further basis for distinguishing the Sunectnineteen variety from its seed parent, Sunecteight, the variety has been analyzed to obtain an indication of its genetic make-up. Specifically, fruit of the Sunecteight and Sunectnineteen varieties was electrophoretically analyzed on starch gel using the staining and electroporetic procedure that was set out in Bruce D. Mowery et al., Inheritance of Isocitrate Dehydrogenase, Malate Dehydrogenase, and Shikimate Dehydrogenase in Peach and Peach×Almond Hybrids, J. American Hort. Soc. 115 (2): 312–319 (1990). Malate dehydropenase staining was performed using a Morpholine-citrate pH 6.1 system. The isoenzyme separation and banding patterns for Malate dehydrogenase (MDH) are srikingly different for the Sunecteight and the Sunectnineteen varieties. The banding pattern of Nuectnineteen in FIG. 2 is quite rare and is present only in about 2% of all peach and nectarine varieties.

The results of the electrophoretic analysis are set forth in Table 1 below and illustrated in FIG. 2.

TABLE 1

| Malate Dehydrogenase | | |
|---|---|---|
| Average migration in mm. | Sunecteight | Sunectnineteen |
| 33 | H | H |
| 42 | MH | |
| 42.5 | | M |
| 46 | H | |
| 50.5 | MH | |
| 56 | H | |
| 60 | H | |
| 71 | H | H |

(H = heavy staining, MH = medium heavy staining and M = medium staining)

What is claimed is:

1. A new variety of nectarine tree cv. Sunectnineteen as illustrated and described.

* * * * *